United States Patent [19]
Toshima et al.

[11] Patent Number: 5,585,729
[45] Date of Patent: Dec. 17, 1996

[54] FLUID CONCENTRATION DETECTING APPARATUS

[75] Inventors: Masato Toshima, Sunnyvale; Hiroji Hanawa, Santa Clara; Jerry Wong, Fremont, all of Calif.

[73] Assignee: Gamma Precision Technology, Inc., Santa Clara, Calif.

[21] Appl. No.: 61,713

[22] Filed: May 13, 1993

[51] Int. Cl.$^6$ .................................................. G01R 33/00
[52] U.S. Cl. ........................... 324/445; 324/204; 324/715; 204/406; 422/82.02
[58] Field of Search ................................ 204/406, 153.1; 422/82.02, 76; 324/204, 445; 437/8

[56]  References Cited

U.S. PATENT DOCUMENTS

| | | |
|---|---|---|
| 2,435,043 | 1/1948 | Lehde et al. . |
| 3,355,661 | 11/1967 | Nonaka .................................. 324/445 |
| 3,433,057 | 3/1969 | Halsey . |
| 3,940,996 | 3/1976 | Lauhoff et al. . |
| 4,282,487 | 8/1981 | Warren .................................. 324/445 |
| 4,380,924 | 4/1983 | Nakamoto et al. . |
| 4,581,942 | 4/1986 | Ogura et al. . |
| 4,590,424 | 5/1986 | Girot .................................... 324/204 |
| 4,630,482 | 12/1986 | Traina . |
| 4,850,220 | 7/1989 | Asano et al. . |
| 4,918,979 | 4/1990 | Pearce et al. . |
| 4,958,523 | 9/1990 | Knaak . |
| 4,983,270 | 1/1991 | Kikuta et al. . |
| 5,001,424 | 3/1991 | Kellett .................................. 324/204 |
| 5,005,402 | 4/1991 | Pischinger et al. . |

FOREIGN PATENT DOCUMENTS

| | | | |
|---|---|---|---|
| 0913202 | 3/1982 | U.S.S.R. | .................................. 324/445 |

*Primary Examiner*—Maura K. Regan
*Assistant Examiner*—Jose M. Solis
*Attorney, Agent, or Firm*—Hickman Beyer & Weaver

[57] ABSTRACT

An apparatus is disclosed for determining the concentration of a fluid. In one aspect of the invention an apparatus for detecting the ionic concentration of a fluid is provided. The ionic concentration detecting apparatus may include a resonance coil or other suitable receiver that arranged to be influence by the fluid being monitored. The resonance coil is driven by a high frequency signal having a frequency in the range of 10–100 MHz. A detector is provided to measure the losses experienced by the resonance coil. In another aspect of the invention, an ultrasonic based density detecting apparatus for detecting the density of the fluid is provided. The ionic concentration detecting device may be used in conjunction with the density determining device to provide concentration detecting capabilities for solutions having multiple constituents. One particularly beneficial application of the invention is for determining the concentration of an acidic solution used in a wafer wet cleaning step of a semiconductor fabrication process.

31 Claims, 6 Drawing Sheets

FLUID CONCENTRATION DETECTING APPARATUS

BACKGROUND OF THE INVENTION

The present invention relates generally to devices for monitoring the concentration of a fluid.

In semiconductor fabrication, wet cleaning and wet etching are critical steps in the fabrication process. Typically a strong acid such as Hydrofluoric acid (HF), buffered HF (HF & $NH_4F$), Sulfuric acid, ($H_2SO_4$), Nitric acid ($HNO_3$) or a combination of different acids are used as cleaning solution. Using an acid having the wrong concentration or the wrong composition will cause significant reduction in the yield of the fabrication process. In order to maintain optimal cleaning, it is important to maintain the concentration level within certain control limits. However, the concentration of the acidic material will often dilute somewhat during use and this results in insufficient cleaning. Accordingly, it is common to frequently replenish the cleaning solution in batch process methods and to maintain a continuous flow of fresh cleaning solution in continuous cleaning methods.

In semiconductor fabrication, wet cleaning and wet etching of the wafers are very critical steps in the fabrication process. One specific cleaning operation is to remove native silicon dioxide ($SiO_2$) from silicon surface. The silicon dioxide is naturally formed when the silicon is exposed to oxygen in the air. To remove silicon dioxide a cleaning solution that includes a mixture of hydrofluoric acid (HF) and ammonium fluoride ($NH_4F$) is used. The mixture ratios typically vary in the range of 1:30 to 1:6 depending on the application. However, it is very important to control the etching rate. Since the process is typically controlled by time, if the etching rate of $SiO_2$ is too fast, it will cause over etching of base silicon material. Such over etching can alter the characteristics of the electronic components being formed.

Presently, there are no good methods of monitoring the concentration of the solution on a continuous basis during use. Accordingly, a common practice is to periodically clean a test wafer and to measure the actual amount of etching that occurs on the test wafer. The concentration can then be adjusted accordingly. Unfortunately, this is a time and labor consuming process and it also cannot detect any problems that arise between wafer tests. Accordingly, there is a need for a device which can monitor the solution and predict the associated etch rate.

As the manufacturing requirements for large scale integrated circuits become more exacting, new requirements will emerging such as side wall oxide removal. In this process, a weak concentration of acid is used. The weak concentration is used because the material to be etched is so thin that it is crucial to stop etching at a specific point. Accordingly, high concentration solutions are not adequate. However, low concentration solutions tend to deteriorate very quickly (i.e. with only a small amount of etching). Accordingly, current practice utilizes a premixed chemical which is showered over the wafers and drained to the waste tank. However, due to environmental concerns, the costs of such waste disposing is increasing. Therefore, there is a need for a system capable of monitoring solutions having a very weak concentration in an in-line mode without causing any contamination. However, there are no such techniques available currently.

There are two major problems posed by such systems. The first problem is that two different chemicals must be independently detected within an aqueous solution. A single variable detection scheme can not be used to determine the concentration of two different chemicals. The second problem is that existing systems can not provide continuous in-line monitoring without contaminating the solution. In practice, the conventional methods of monitoring concentration levels of a highly corrosive acid solutions are not well suited for monitoring on a continuous basis. The reason is that it is difficult to find contacts and/or electrodes that both work well for their intended function and will not corrode appreciably. In many cases, any corrosive action will be detrimental to both the probes themselves and the cleaning solution. The drawbacks as far as the cleaning solution is concerned is that the dissolved probe material tends to pollute the cleaning solution. The drawback from a probe's standpoint is that their accuracy tends to deteriorate with the corrosion and replacement costs are typically relatively high.

In view of these drawbacks, in most current semiconductor fabrication applications, the concentration of the cleaning solution is not controlled other than to control the concentration of the initial mixture of water and acid. Indeed, the original concentration of the acid (as it is bought from chemical vendors) is not even checked in many cases. Degradation in the cleaning solution and variations in the concentrations are not monitored in any manner during use. Thus, the cleaning solution changing intervals are typically determined on the basis of experience as to what statistically tends to work. In many cases, due to the lack of concentration information, the cleaning solution is prematurely discarded. In a semiconductor fabrication line, the disposal costs of these strong acids account for more than 60% of the total disposal cost and cost savings in this area are becoming more important.

There are currently a variety of practices for measuring acid concentration levels. For example, pH meters can determine ionization to a very accurate resolution. However, the sensor tips are typically made from hygroscopic silica will corrode extensively in strongly acidic solutions such as hydrofluoric acid. Accordingly, they cannot be used for continuously monitoring the cleaning solution. Another common practice is to use a resistivity meter which measures the conductivity of liquid by determining the resistivity between two electrodes that are wetted in the liquid. Resistivity measurement is good for low concentration measurements. However, such measurement are susceptible to temperature and electrodes condition. Selection of a material suitable for use as the electrode is extremely difficult when the solution to be monitored includes a strong acid such as HF. A third common practice is to use a refractometer which measures changes in the refractive index to determine concentration variations in certain aqueous solutions. With hydrofluoric acid, such measurements have the ability to measure concentrations variations on the order of 0.1%. However, again, the prism, which is made of glass or sapphire, is corroded by strong acids such as HF. Accordingly, such monitoring devices are not suitable for continuous monitoring.

Although the described wafer cleaning example is one very good example of an application which requires a non-invasive monitoring of acid concentration levels, it should be appreciated that there are a wide variety of other applications that share the same problems. Accordingly, there is a need to develop an alternative acid concentration detecting apparatus which does not necessarily require contact between the potentially corrosive components of the sensing apparatus and the acid solution.

SUMMARY OF THE INVENTION

Accordingly, it is an object of the present invention to provide an improved apparatus and method of determining the concentration of an aqueous solution without causing any contamination of the solution provide in-line and which can be used in continuous monitoring environments.

To achieve the foregoing and other objects and in accordance with the purpose of a first aspect of the present invention, an apparatus for detecting the ionic concentration of a fluid is provided. The ionic concentration detecting apparatus includes a housing arranged to receive a tube that is capable of passing the fluid there through. A signal generator for providing a high frequency excitation signal. In a preferred embodiment, the signal generator provides a signal having a frequency in the range of 10–100 MHz. An excitation coil is electrically connected to the signal generator and is wrapped around a portion of the tube. A resonance coil is wrapped around another length of the tube such that the resonance coil and the excitation coil are arranged for inductive communication. A detector is provided to measure the losses experienced by the resonance coil.

In a preferred embodiment, the excitation coil is wrapped around the tubing adjacent a first end of the resonance coil and the detector is a detection coil wrapped about the tubing adjacent a second end of the resonance coil. The resonance coil is also coupled to a capacitor means to form an LC circuit. In a more preferred embodiment, the LC circuit is tuned to match the frequency outputted by the signal generator when a reference fluid is passed through the tubing.

In another preferred embodiment, a rigid clamp formed from a dielectric material is provided to rigidly support the tubing. The tubing itself is formed from a dielectric material that has very good resistance to corrosion. Additionally, the housing forms an electrical shield for the various electrical components. In alternative embodiments, the apparatus may take the form of a self contained device having its own built in tubing, or may be arranged to clamp onto existing piping.

In an alternative aspect of the invention, an apparatus for detecting the density of a fluid is provided. The density determining device includes a housing having an inlet, an outlet and a sensing chamber therein. A pair of acoustic plate are positioned at opposite ends of the sensing chamber. Each acoustic plate is coated with a chemically inert material. A transmitter is coupled to one of the acoustic plates and a receiver is coupled to the other. A processor is also provided for determining the density of a fluid passing through the sensing chamber. The processing means receives inputs from a temperature detector that indicates the temperature of the fluid in the sensing chamber, the transmitter, and the receive. It produces an indicia indicative of the density of the fluid being monitored.

In a preferred embodiment, an ionic concentration detecting device is used in conjunction with the density determining device in order to determine the concentration of an ionized solution.

In another aspect of the invention, an apparatus is provided for determining the concentration of an acidic solution used in a wafer wet cleaning step of a semiconductor fabrication process. The apparatus includes an instrument for automatically detecting the ionic concentration of the solution and an instrument for automatically detecting the density of the solution. A processing arrangement is provided for determining the concentration of the wafer cleaning solution based at least in part upon information provided by the ionic concentration detecting means and the density detecting means. The described device can be used to detect the concentrations of a wide variety of solutions including aqueous hydrofluoric acid solutions; solutions including both hydrofluoric acid and nitric acid; solutions including ammonia hydroxide and $H_2O_2$; solutions including hydrochloric acid and $H_2O_2$ and a wide variety of other solutions which include either a single acidic constituent or a combination of constituents.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE INVENTION

The invention will be described in the environment of a concentration detector that is adapted for measuring the concentration of hydrofluoric acid used in a semiconductor wafer wet cleaning process. The presently preferred embodiment of the concentration monitoring device that is adapted for this specific use, operates on the basis of two different principles. Thus, in the described embodiment it includes two major components. The first is an ionic concentration measurement system which in the described embodiment takes the form of an resonance coil based induction loss measuring detector 10. The second major component is an ultrasonic-based sound velocity measurement device 60 which is particularly well adapted to measuring variations in the density of the fluid. Although the combined device has a synergistic effect when used for monitoring the concentration levels of wafer cleaning solutions, in some applications, only one of the two devices may be required.

The induction loss measuring detector is particularly well adapted to measuring concentration levels or concentration variations at very low concentration levels. Initial tests have indicated that such a system is capable of detecting concentration levels to an accuracy on the order of 0.005% in a 2% HF solution. In this system, the acid concentration is measured as ionization efficiency and the measured value is independent of temperature and solution degradation which result from the accumulation of etched material in the solution.

The ultrasonic-based measuring system measures the sound transmission efficiency of the solution, which varies in accordance with the concentration of the total material in the liquid. Thus, changes in the amount of etched material found in the solution can be accurately measured. In a fresh aqueous solution of about 2% HF, initial tests have indicated that the ultrasonic-based system is capable of measuring concentration to an accuracy on the order of 0.02%.

Figure 1:
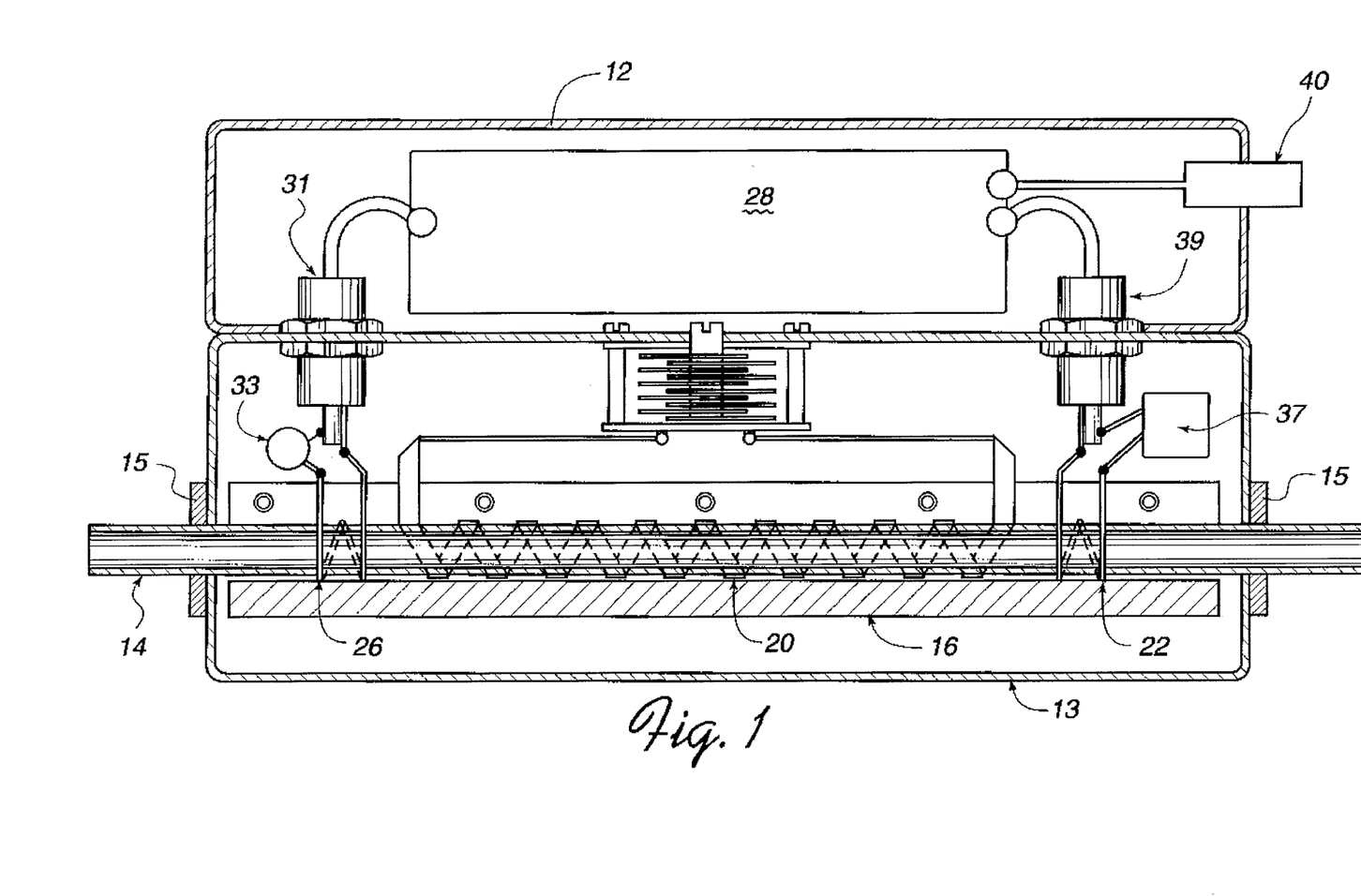
FIG. 1 is a schematic mechanical diagram of a resonance coil based ionic concentration detector in accordance with the present invention.

Turning initially to FIG. 1, a preferred embodiment of the ionic concentration detector 10 will be described in more detail. As seen in the figure, the concentration detector includes a signal generator, an transmitter adapted to apply the signal to the vicinity of the fluid whose concentration level is to be detected, a resonance coil 20, a detector 22, and a signal amplifier 38. In the preferred embodiment shown, the transmitter takes the form of an excitation coil 26.

The ionic concentration detector 10 of the described embodiment is contained within a housing 12 that includes a casing 13 having a tube 14 passing there through. During use, the fluid to be monitored is passed through the tubing 14. The housing 12 is intended to form an electrical shield to prevent noise from adversely affecting the measurements. By way of example, a suitable material for the housing 12 is aluminum. Pipe supports 15 are provided adjacent the tube's entrance to and exit from the housing 12 and a clamp 16 is provided within the case to support the pipe. The pipe supports 15 and clamp 16 are intended to cooperate to rigidly support the pipe in a manner which will keep it from moving relative to the housing 12. This is important since movement of the tubing after calibration can significantly impair the detectors accuracy and movement of the tubing during use would destroy its precision. The clamp 16 is formed from a hard plastic dielectric material such as Delrin. At the frequency levels at which the system is used, it is very sensitive to small changes in inductance and capacitance. The sensitivity is such that mechanical movements of the electrical wires or components will vary the inductance or capacitance sufficiently to influence the systems accuracy. Thus, it is important that the clamp and pipe supports hold the tubing firmly in place.

The tubing 14 is preferably formed from an inactive, dielectric material that will not be corroded by the fluids passing there through. By way of example, a suitable material is Teflon. As indicated above, one specific application for the present invention is its use in monitoring the concentration of hydrofluoric acid (HF). Hydrofluoric acid is extremely corrosive and thus the use of a truly inactive material such as Teflon is important for such applications. However, it should be appreciated that the invention can work with a wide variety of different tubing.

One advantage of the described arrangement is that the ionic concentration detector can be mounted on installed nonconductive tubing as a clamp on sensor. This permits the ionic concentration measuring device to be used in retrofitting operations. A disadvantage of such an arrangement is that it would be very difficult to obtain the absolute concentration level using previously installed piping, since the pipes influence on the signal would be difficult to determine. However, such an arrangement, can be very advantageously used to determine relative ionization levels. Further, if such a device is used in conjunction with a stand alone device for initial calibration, the problem of a lack of absolute measurements can be eliminated.

The ionic concentration detector 10 includes a signal generator, a resonance coil 20, a signal detector 22 and a signal processing arrangement 23. The signal generator includes an oscillator 24 which outputs a high frequency signal to an excitation coil 26. Although the device can be configured to work at a wide range of frequencies, the applicant has found that frequencies in the range of approximately 10 to 100 MHz work quite well. Frequencies in the range of approximately 30 to 80 MHz work particularly well with a frequency of 50 MHz being suitable in most implementations that are used with aqueous solutions.

The signal generator is mounted on a printed circuit board 28 and is coupled to the excitation coil 26 via a coaxial connector 31. A high pass filter 33 is provided at the connection to insure that only the desired signal is transmitted. In one actual embodiment, the high pass filter takes the form of a diode 33. The excitation coil 26 is wrapped around the tubing 14 adjacent a first end of the resonance coil 20. The excitation coil 26 acts as the primary coil in a transformer and its signal is inductively transferred to resonance coil 20.

The resonance coil forms part of an LC circuit tuned to the frequency outputted by the oscillator with a reference solution in the tubing. In most cases, the reference solution is pure water. Thus, the resonance coil is coupled to a capacitor 35. The resonance coil 20 is wrapped around the exterior of a tube 14 which receives the fluid to be monitored. Experience has shown that when the resonance coil is wrapped around the flow tube 14, the fluid passing through the resonance coil acts much like a transformer core. When the fluid is ionized, the losses will increase quickly with even very small increases in the ionization concentration. This causes drift in the resonance frequency and transmission efficiency degrades quickly. This results in a lower signal strength at the detection coil. The actual mechanism which causes the losses is not fully understood. One hypothesis is that ionized particle in the presence of a high inductive field causes increased eddy current losses. In any event, the magnitude of the losses are quite consistent for a given ionization level in a given fluid. The magnitude of the losses also seems to be relatively independent of temperature variations and density variations caused by the accumulation of pollutants (etched materials) or any non-ionizing agents such as alcohol in the cleaning solution.

A detection coil 22 is wrapped around the tube 14 adjacent the second end of the resonance coil 20. Thus, the detection coil effectively inductively monitors the losses that occur in the resonant circuit. A signal multiplier 37 converts the alternating signal detected by the detection coil 22 to a direct current signal. A connector 39 that may take the form of a coaxial connector couples the signal multiplier 37 to the printed circuit board 28 which also houses an amplifier 38. The amplified rectified signal is then passed through a connector 30 to the signal processing electronics 23.

Figure 2:
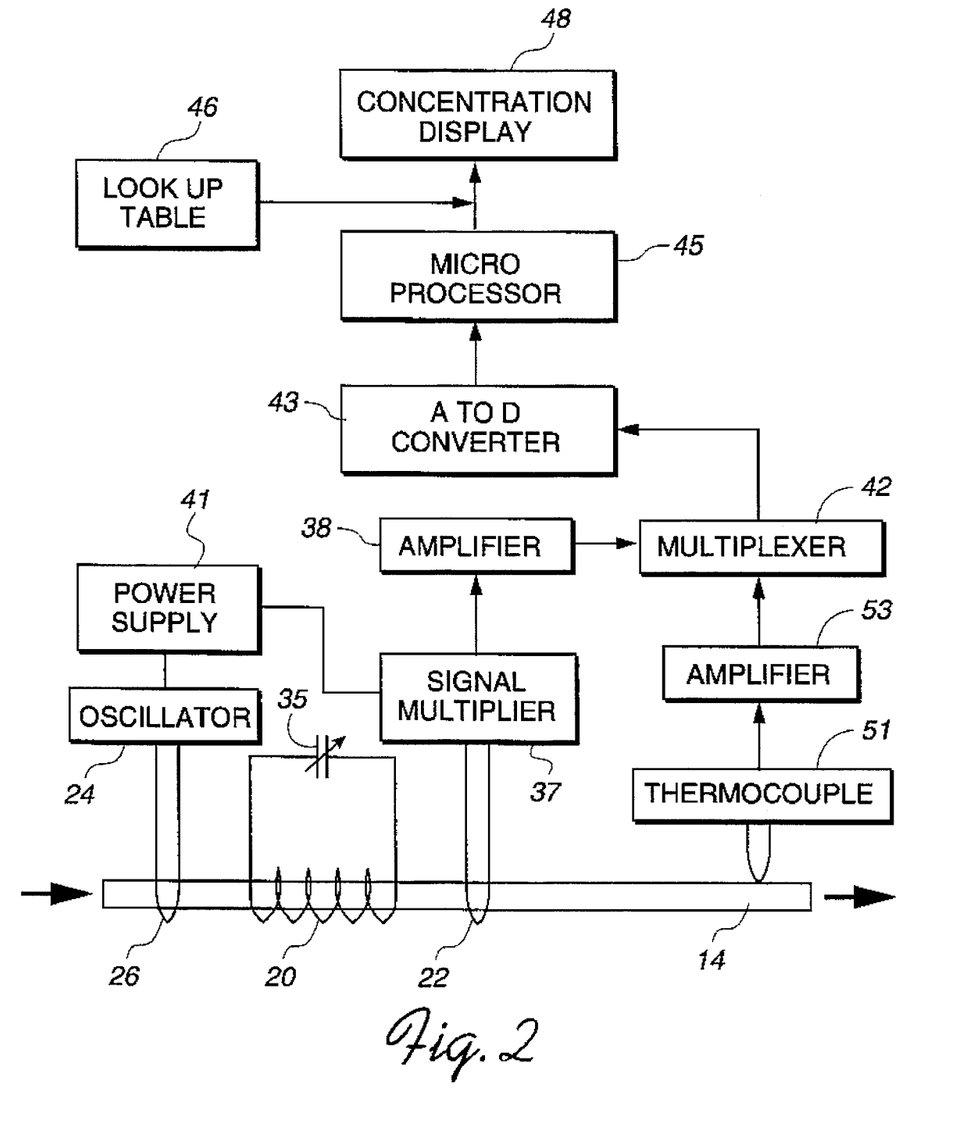
FIG. 2 is a schematic electrical block diagram of the ionic concentration detector shown in FIG. 1.

The electronic layout of the inductive concentration measuring component 10 will be described in more detail below with reference to FIG. 2. As seen therein, the electronics, including oscillator 24 is powered by a power supply 41. As indicated above the oscillator outputs a signal having a frequency in the range of 10 to 100 MHz. By way of example 50 MHz works well for aqueous solutions. The high frequency signal generated by the oscillator is applied to excitation coil 26 where it is inductively transferred to the resonance coil 20. The resonance coil 20 cooperates with capacitor 35 that is mounted to the housing to form an LC circuit tuned to the oscillator frequency with pure water in the tubing. From the resonance coil 20, the signal is inductively transferred to the detection coil 22. Thus, the detection coil can be used to effectively monitor the losses that occur within the resonance coil.

The signal picked up by detector coil 22 is then convened to a direct current signal by signal multiplier 37, amplified by an amplifier 38 and passed through a multiplexer 42 to an A/D converter 43. The A/D converter 43 converts the analog signal into a digital signal that is indicative of the magnitude of the signal received by detector 22. The digital signal outputted by A/D converter 43 is inputted into a microprocessor 45 which is programmed to process the data received appropriately. One suitable method would be to use a Look up table 46 to determine the fluid concentration level based upon the magnitude of the signal received by the A/D converter. The result can then be outputted in any desirable fashion. In feedback type control systems, the microprocessor could be arranged to automatically control the rate at which the fluid is replenished or replaced. Additionally or alternatively, the result can be displayed or stored in any suitable form. By way of example a digital or dial type display 48 could be provided to indicate the ionic concentration of the fluid. The A/D converter 43 and microprocessor 45 constitute part of the signal processing electronics 23 which are typically found in a computer located outside of housing 12.

In experiments conducted by the applicants, the magnitude of the losses generated by the described arrangement seem to be quite independent of temperature. Again, the explanation for this occurrence are not really understood. However, for a variety of reasons, it may be desirable to know the temperature of the fluid passing through the concentration measuring apparatus 10. Accordingly, a thermocouple 51 may be provided to monitor the temperature of the liquid itself, or the temperature of the tubing immediately adjacent the fluid. The temperature signal provided by the thermocouple 51 is amplified by an amplifier 53 and passed to the multiplexer 42 which passes the temperature signal to the A/D converter 43. From A/D converter 43, the temperature measuring signal is passed in digital form to microprocessor 45.

The various electronic components such as the amplifiers 38 & 51, the multiplexer 42, A/D converter 43, and microprocessor 45 are all mounted on the printed circuit board 28 in the described embodiment. However, it should be appreciated that the an external controller or signal processor could be readily substituted. Similarly, the actual components used to process and/or interpret the signal(s) can be readily varied.

When the solution passing through tube 14 is has an ionization ratio that is near zero., (such as pure water) it apparently acts as a rather good insulator and the losses that occur in the resonance coil can be used for the purposes of calibration. On the other hand, when the solution passing through the tube is ionized even slightly, the losses increase very quickly. Thus, by monitoring the loss level, the detector 10 can be used to accurately measure the ionization ratio of the fluid which in turn translates to the concentration of the acid. The accuracy is particularly good at low ionization levels. It is suspected that this loss may be due to increased eddy current losses in the liquid. As indicated above, the detection sensitivity appears to be independent of temperature variations. However, the system's sensitivity increases as the frequency increases. Thus, by way of example, in the described embodiment, a 50 MHz frequency is used with frequencies in the range of 10–100 MHz forming a preferred range.

Figure 3:
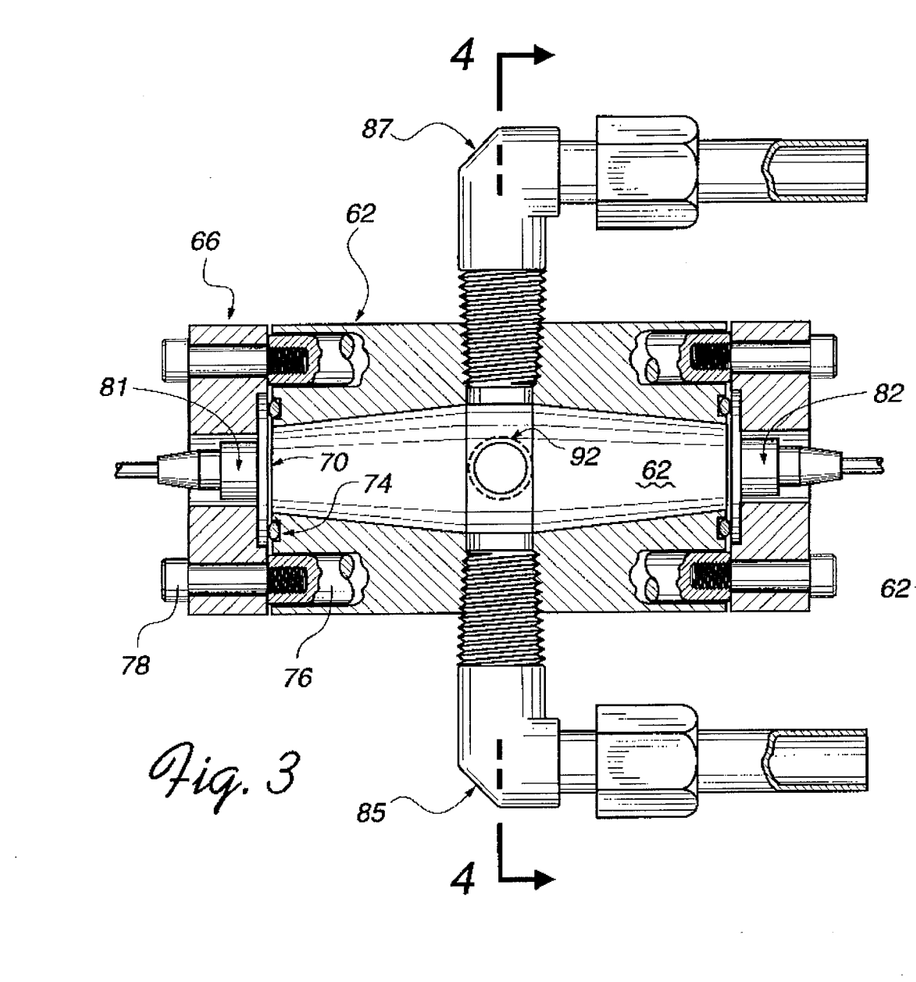
FIG. 3 is a cross sectional side view of a ultrasonic concentration detector in accordance with the present invention.
Figure 4:
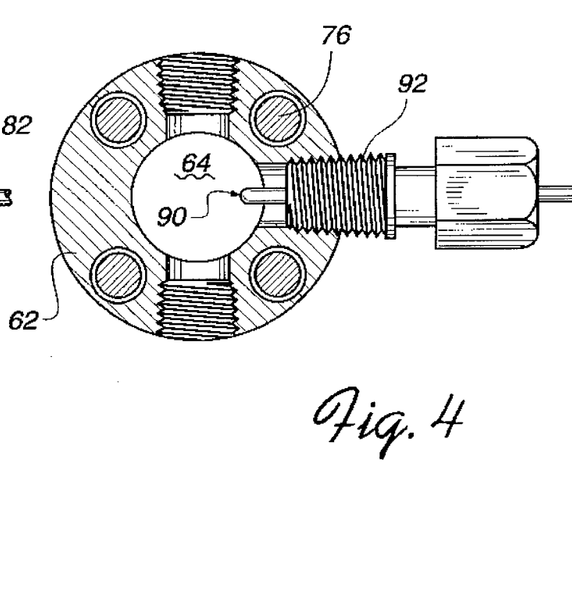
FIG. 4 is a cross sectional side view of the concentration detector shown in FIG. 3 taken along line 4—4.
Figure 5:
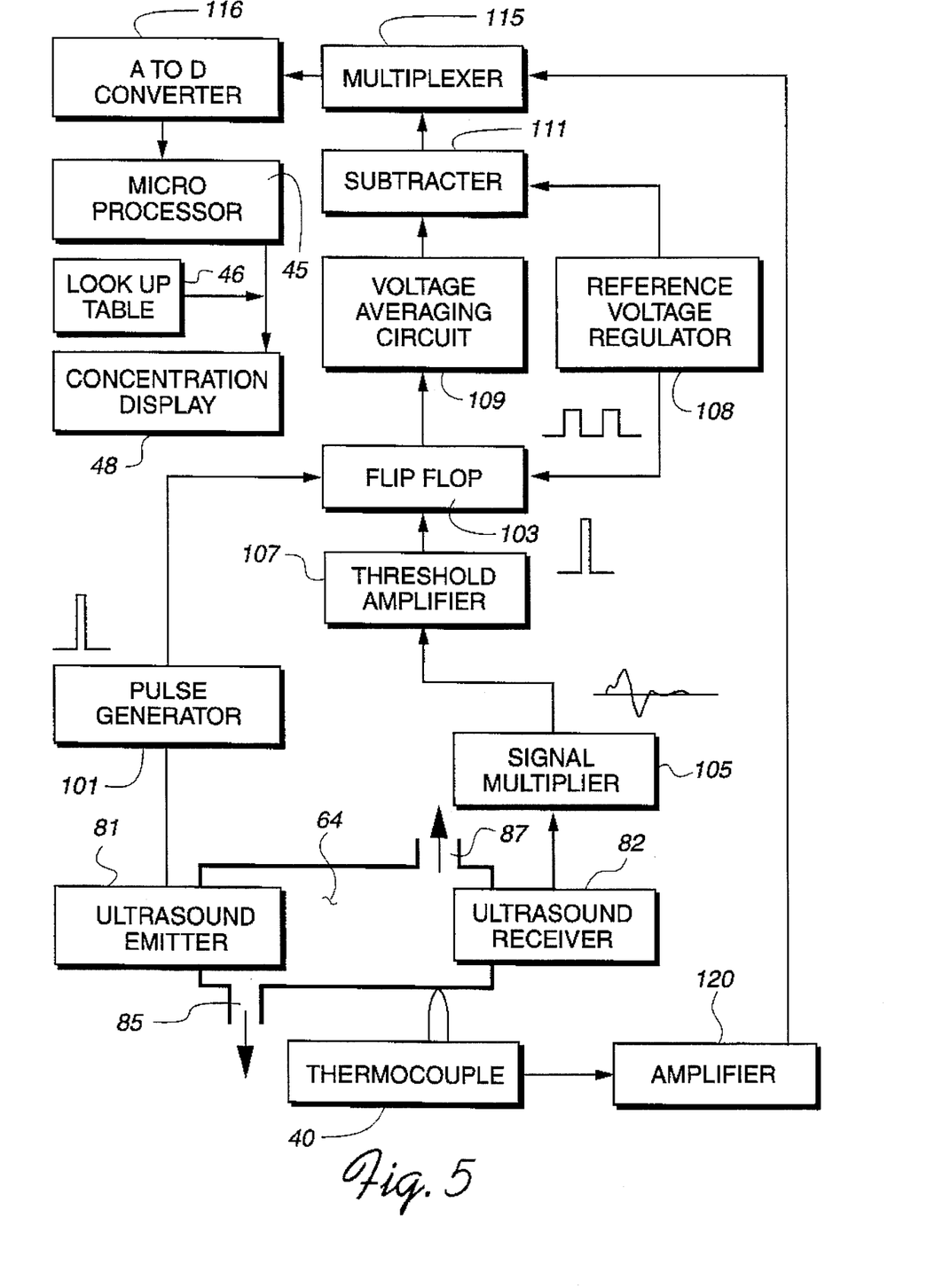
FIG. 5 is a schematic electrical block diagram of the ultrasonic concentration detector in accordance with the present invention.

Referring next to FIGS. 3–5, the ultrasonic concentration measuring component of the preferred embodiment will be described. Initially, a suitable layout will be described with reference to FIG. 3. The ultrasonic fluid sensor 60 has a housing 62 having a sensing chamber 64 therein. The sensing chamber 64 is generally elongated and is tapered such that its center portion is wider than its end portions. The bulge is to insure that any bubbles that enter the sensing chamber will quickly rise to the outlet and pass out of the chamber. This is done since bubbles would adversely influence the ultrasound transmissions. Similarly, any debris will fall to the inlet. The housing 62 is formed of a inactive material such as Teflon that will not be corroded by the acid that is being monitored. A pair of ring shaped end plates 66 are coupled to opposing ends of the housing 62. The end plates have facing grooves 68 which receive acoustic plates 70. The acoustic plate is sealed by the O-rings 74. Thus, the acoustic sensing chamber 64 is formed between the acoustic plates 70. The O-rings are preferably formed from a material that is chemically inert and clean in strongly acidic solutions such as hydrofluoric acid (HF), sulfuric acid ($H_2SO_4$) and nitric acid ($HNO_3$). By way of example, a suitable O-ring material is Chemraz 505 manufactured by Greene Tweed, Inc. of California, U.S.A.

In order to maintain a fixed distance between the acoustic plates, a set of four studs 76 extend longitudinally through the housing in parallel with the sensing chamber 64. The end plates are then attached to the housing 62 by bolts 78 which threadably engage the studs 76. The studs are formed from a material that is very stable thermally. By way of example, a suitable material is INVAR. By using thermally stable studs, errors caused by thermal expansion of the detector are significantly reduced. To maximize performance, it is also important to keep the receiver and the transmitter parallel and concentric since the ultrasonic signal is emitted perpendicularly to the surface and has very acute directionality. The described arrangement accomplishes this requirement very well.

A ultrasonic emitter 81 is mounted on one end of the sensing chamber 64 and a ultrasonic receiver 82 is mounted on the opposite end. The ultrasonic emitter and receiver may take the form of piezoelectric devices. The emitter and receiver are attached to their respective acoustic plates 70. The acoustic plates are made from an acoustically absorbent material. In the described embodiments, the acoustic plates are thin graphite plates formed from vitreous carbon (also known as glassy carbon). The inner surface (i.e. the surface exposed to the sensing chamber) is coated with a very thin layer of a chemically inert and clean material such as fluorocarbon. By way of example, PVDF works well since when it is coated in a thin film, it has a low porosity. Although Teflon has better corrosion resistance characteristics, it has a higher porosity. The ultrasonic emitter and receiver are protected by an insulating material which is intended to absorb vibrations.

The inlet fitting 85 is provided at the lower side of the sensing chamber 64 and the outlet fitting 87 is provided at the upper end of the sensing chamber. A temperature sensor 90 is introduced to the sensing chamber 64 through a fitting 92 positioned radially half way between the inlet and outlet. The temperature sensor is mounted so that the liquid in the sensing chamber will always be in contact with the tip of the sensor. The temperature sensor may take the form of any suitable conventional sensor such as a resistive temperature device (RTD). All surfaces of the fittings are also formed from an inactive material such as Teflon. Thus, all surfaces that are exposed within the sensing chamber are coated with an inactive material.

The velocity of the sound passing through the sensing chamber 64 will vary as a function of changes in the concentration. Of course, the velocity is also quite dependent on the liquid temperature.

Referring next to FIG. 4, the electrical layout of the ultrasonic concentration measuring probe 60 will be described. A pulse generator 101 generates a stream of pulses at predetermined intervals. The pulse is transmitted both to the ultrasound emitter 81 and a flip flop 103. The signal stimulates the piezoelectric element in the emitter, which in turn propagates the vibration induced by the pulse to the associated acoustic plate 70. The acoustic plate propagates an ultrasonic signal which passes through the liquid in the sensing chamber 64. The signal is then picked up by the ultrasonic receiver 82. The receiver transmits an electrical signal to signal multiplier 105. A representative potential waveform is shown in FIG. 5. The multiplied signal is then passed to a threshold amplifier which outputs a signal indicative of the moment that the amplitude of the multiplied signal exceeds a predetermined threshold. The output of the threshold amplifier 107 is also feed as an input to flip flop 103.

The flip flop 103 has two inputs. The first is the pulse generator 101 and the second is threshold amplifier 107. Thus, the output of flip flop 103 is a pulse train wherein the width of the pulses is indicative of the time lag between the emission and the detection of the ultrasonic signal in the sensing chamber. The amplitude of the pulse train is determined by a reference voltage provided by reference voltage regulator 108. The pulse train output by flip flop 103 is feed into a voltage averaging circuit 109 and passed to a subtractor 111 where it is subtracted from a reference voltage supplied by the voltage regulator 108. The output of the subtractor is then passed through a multiplexer 113 on to an A/D converter 116 and microprocessor 45. The microprocessor is programmed to calculate and/or look up the concentration and display the results on display 48. Again, in feedback control systems, the microprocessor 45 could also be used to orchestrate the system control.

Since temperature is important to the concentration calculations when ultrasonic concentration measurements are made, the output of thermocouple 90 is amplified by an amplifier before being passed to multiplexer 113. From multiplexer 113, the temperature measurement signal is also passed through A/D converter 116 on its way to microprocessor 45. This information is used to calibrate the concentration calculations on the basis of temperature.

Figure 6:
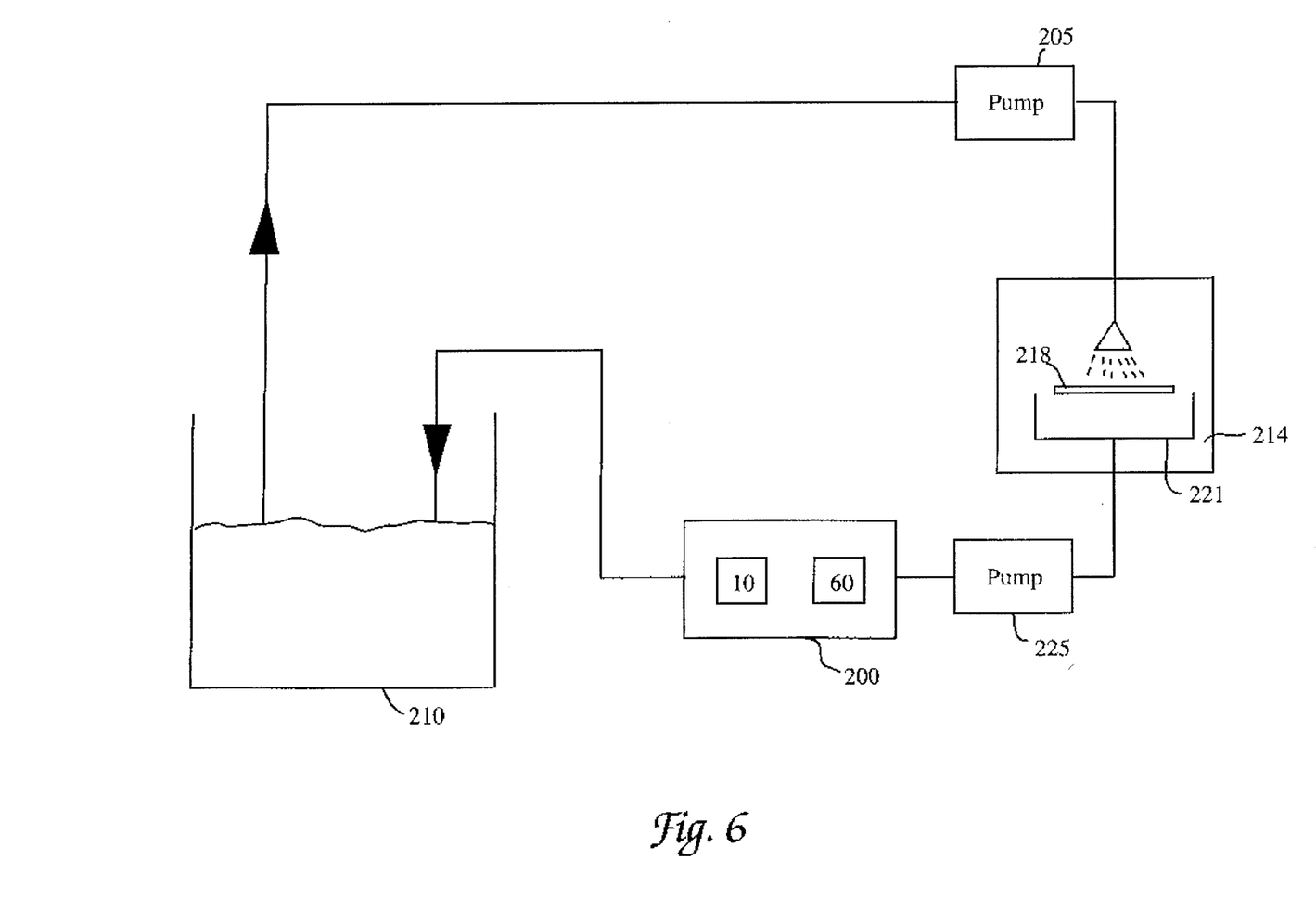
FIG. 6 is a schematic diagram of a solution concentration monitoring arrangement in accordance with the present invention.

Although each of the described concentration detecting instruments works well independently in some situations, it has been determined that their use in combination has synergistic effects as well. For example, in one application illustrated with reference to FIG. 6, a concentration measuring instrument 200 incorporates both an ionic concentration measuring device 10 and an ultrasonic density measuring device 60. In the embodiment shown, these are combined in series into a single concentration detecting instrument 200.

The concentration detecting instrument 200 can be used for continuous in-line monitoring of a solution such as a cleaning solution in semiconductor wafer fabrication processes. In the embodiment shown in FIG. 6, the concentration detecting instrument 200 is used to monitor the concentration of an acidic solution used for etching wafers. A pump 205 pumps the aqueous solution from storage tank 210 and through a cleaning/etching chamber 214 where it is sprayed over a wafer 218. The spayed materials are collected in a collection tank 221 and a pump 225 is used to pump the solution through a concentration detecting instrument 200. The concentration detecting instrument 200 is then used to evaluate the solution. After the solution is evaluated, it is returned to storage tank 210. In this manner the quality and concentration of the solution in the tank can be monitored. In an alternative embodiment, the actual (conventional) etching and/or cleaning steps may be carried out in a separate loop from the solution monitoring loop.

Figure 7:
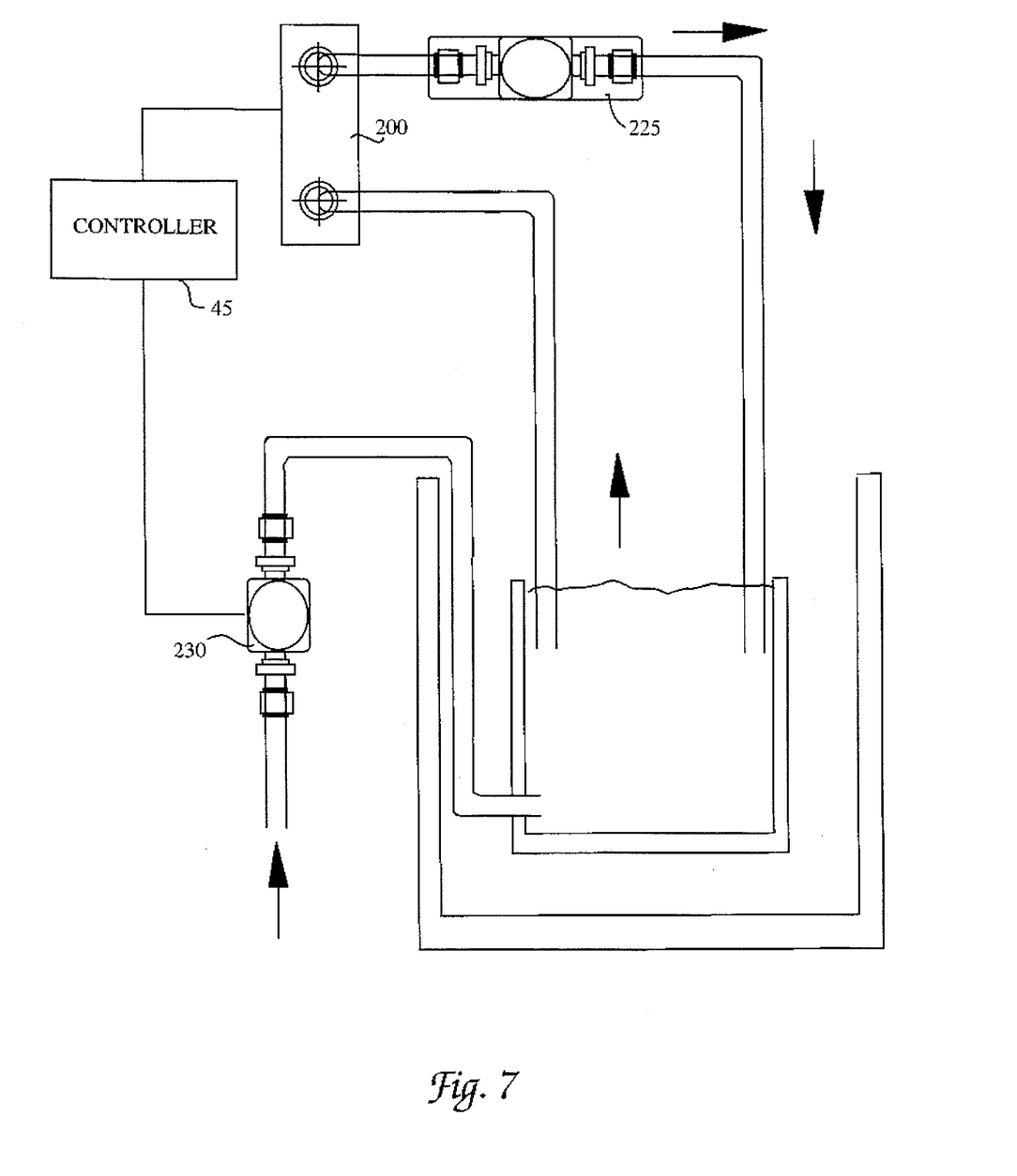
FIG. 7 is a schematic diagram of a solution concentration controlling arrangement in accordance with the present invention.

Referring next to FIG. 7, a system that incorporates feedback control will be briefly described. In this embodiment, a separate loop is used to monitor the aqueous solution in storage tank 210. A pump 225 is used to pump the solution through the concentration detecting instrument 200. The controller (which may take the form of microprocessor 45) is used to control one or more valves 230 that allow additional materials to be added to the storage tank 210. The additional materials may be any suitable material, including deionized water, acid or any other suitable chemicals. Of course, in an alternative embodiment, the concentration detecting instrument 200 can be used in-line with the cleaning, etching or other working loop. In other embodiments, the controller can be used to control the length of an etching, soaking, rinsing or other such step.

By way of example, one good application of the present invention is to monitor the of the cleaning solution used in a wafer cleaning process commonly referred to as an "RCA cleaning" process in the trade. The RCA process was initially proposed by Mr. W. Kern of RCA in approximately 1970. By way of example, a typical cleaning process initially soaks the wafer in a solution that includes $NH_4OH$: $H_2O_2$:$H_2O$ mixed in a ratio of approximately 1:1:5. The wafer is soaked for 10 minutes at a temperature of 80° C. The wafer is then rinsed with deionized water. The rinsed wafer is then etched with a 1% aqueous solution of hydrofluoric acid (HF) and rinsed again with deionized water. The wafer is then soaked in a solution of HCl: $H_2O_2$:$H_2O$ at 80° C. for 10 minutes before it is again rinsed with deionized water and spun dry.

The described RCA cleaning process is known to be effective for removing metallic and organic contamination on a silicon wafer. However, the composition of the solution degrades very quickly after mixing. Thus, the etching and soaking time vs. solution concentration controls are very critical. The described concentration detecting instrument 200 is ideal for monitoring such solutions. Specifically, the described ionic concentration detector 10 is quite sensitive to $NH_4OH$ and HCl. However, it is not particularly sensitive to $H_2O_2$. On the other hand, the ultrasound measuring device can measure the sum of $NH_4OH$ and the $H_2O_2$ or the sum of the HCl and the $H_2O_2$. Thus, by subtracting the determined amount of $NH_4OH$ (or HCl) as determined by the ionic concentration measuring device from the sum determined by the ultrasound measuring device, the concentration of the $H_2O_2$ can also be determined.

A similar synergistic effect is found when measuring the concentration of combined acid solutions as well. By way of example, consider the example of an aqueous solution that includes a mixture of HF and $HNO_3$. The ionic concentration measuring device 10 can determine the combined ionic concentration. At the same time, the ultrasound measuring device can determine the combined density. Thus, the percentages of each can be determined since there are two variables and two unknowns. For example, in a given unknown system, the concentration of HF is an unknown X% and the concentration of $HNO_3$ is an unknown Y%. However, the total calculated density A will be equal to a constant ($a_1$) times X plus a constant ($a_2$) times Y. At the same time, the total calculated ionization B will be equal to a constant ($b_1$) times X plus a constant ($b_2$) times Y. That is:

$$A = a_1 X + a_2 Y$$

$$B = b_1 X + b_2 Y$$

The values A and B are calculated by the concentration detecting instrument 200 and the constants $a_1$, $a_2$, $b_1$ & $b_2$ are all constants that are specific to each given chemical at a given temperature. Accordingly, since there are only two unknowns (X & Y), the concentration of both constituents, (i.e. the HF and the $HNO_3$) can be determined.

Although only a few embodiments of the present invention have been described herein, it should be understood that the present invention may be embodied in many other specific forms without departing from the spirit or scope of the invention. For example, although the ionic concentration detection device has been described in terms of an embodiment that employs a resonance circuit, it should be appreciated that alternative receivers could be used, so long as the strength of the signal received by the receiver is affected by the level of ionization in the fluid passing through the tube. Therefore, the present examples are to be considered as illustrative and not restrictive, and the invention is not to be limited to the details given herein, but may be modified within the scope of the appended claims.

We claim:

1. An apparatus for detecting the ionic concentration of a fluid, the apparatus comprising:

a housing arranged to receive a tube that is capable of passing the fluid there through, the tube having a longitudinal fluid flow axis;

a signal generator for providing a high frequency excitation signal;

an excitation coil wrapped around a portion of the tube, the excitation coil being connected to the signal generator such that the high frequency excitation signal may be applied to the excitation coil;

a resonance coil having a plurality of resonance coil turns wrapped around a length of the tube such that an axis of the resonance coil turns is substantially aligned with the longitudinal fluid flow axis, the resonance coil being floating relative to the excitation coil such that the resonance coil is arranged for inductive communication with the excitation coil; and detecting means for measuring losses experienced by the resonance coil.

2. An apparatus as recited in claim 1 wherein the frequency of the signal produced by the signal generator is in the range of approximately 10–100 MHz.

3. An apparatus as recited in claim 1 wherein the frequency of the signal produced by the signal generator is in the range of approximately 30–80 MHz.

4. An apparatus as recited in claim 1 wherein the excitation coil has a plurality of excitation coil turns wrapped around the tubing adjacent a first end of the resonance coil and the detector is a detection coil having a plurality of detection coil turns wrapped about the tubing adjacent a second end of the resonance coil, the excitation and detection coils having associated axes that are substantially parallel with the longitudinal fluid flow axis and the resonance coil axis and the resonance coil being floating with respect to the detection coil such that the detection coil inductively communicates with the resonance coil.

5. An apparatus as recited in claim 1 wherein the resonance coil is coupled to a capacitor means to form an LC circuit.

6. An apparatus as recited in claim 5 wherein the LC circuit is tuned to match the frequency outputted by the signal generator when a reference fluid is passed through the tubing.

7. An apparatus as recited in claim 1 further comprising a rigid clamp formed from a dielectric material, the clamp being arranged to support the tubing.

8. An apparatus as recited in claim 1 wherein the tubing is formed from a dielectric material that has very good resistance to corrosion.

9. An apparatus as recited in claim 1 wherein the housing forms an electrical shield.

10. An apparatus as recited in claim 1 wherein the tubing forms a part of the apparatus.

11. An apparatus as recited in claim 1 wherein the apparatus is arranged to be attached to existing piping and the portion of the piping that the apparatus is attached to forms said tubing.

12. An apparatus as recited in claim 1 wherein the resonance coil is wrapped helically and substantially coaxially around the tube.

13. An apparatus as recited in claim 1 wherein said processing means outputs an indicia indicative of the ionic concentration of the fluid being monitored.

14. An apparatus as recited in claim 13 wherein the processing means includes a signal multiplier that rectifies the signal, an amplifier that amplifies the rectified signal, and a processor for determining said ionic concentration.

15. An apparatus as recited in claim 13 further comprising means for detecting the temperature of the fluid, the temperature detecting means outputting a signal to the processing means.

16. An apparatus as recited in claim 13 wherein the indicia outputted by the processing means includes a control signal arranged to control the concentration of the fluid.

17. An apparatus as recited in claim 13 wherein the indicia outputted by the processing means includes a display signal arranged to display the concentration of the fluid.

18. An apparatus as recited in claim 13 wherein the indicia outputted by the processing means includes a display signal arranged to display the ionic concentration of the fluid.

19. A apparatus for detecting the ionic concentration of a fluid, the apparatus comprising:

a housing;

a tube that passes through the housing, the tube being capable of passing the fluid there through and having a longitudinal axis;

a signal generator for providing an alternating signal having a frequency in the range of 10–100 MHz;

a resonance coil having a plurality of resonance coil turns wrapped around a length of the tube such that the fluid passing through the tube passes through the turns of the resonance coil;

an excitation coil wrapped around a portion of the tube adjacent a first end of the resonance coil such that the fluid passing through the tube passes through turns of the excitation coil, the excitation coil being connected to the signal generator and arranged for inductive communication with the resonance coil;

a detection coil wrapped about the tubing adjacent a second end of the resonance coil such that the fluid passing through the tube passes through turns of the detection coil, the detection coil being arranged for inductive communication with the resonance coil, the resonance coil being floating with respect to both the excitation and detection coils;

capacitor means coupled to the resonance coil to form an LC circuit; and processing means for processing the detected signal and outputting an indicia indicative of the ionic concentration of the fluid being monitored.

20. An apparatus as recited in claim 19 wherein the LC circuit is tuned to match the frequency outputted by the signal generator when a reference fluid is passed through the tubing.

21. An apparatus as recited in claim 19 further comprising:
a rigid clamp formed from a dielectric material, the clamp being arranged to support the tubing; and
wherein the tubing is formed from a dielectric material that has very good resistance to corrosion.

22. An apparatus for detecting the ionic concentration of a fluid, the apparatus comprising:
a housing arranged to receive a tube that is capable of passing the fluid therethrough;
a signal generator for providing a high frequency excitation signal;
a resonance coil wrapped around a length of the tube;
a transmitter connected to the signal generator for transmitting the excitation signal to the resonance coil;
detecting means for measuring the losses experienced by the resonance coil and developing a detected signal representing such losses; and
processing means coupled to said detecting means for determining an ionic concentration of said solution based upon said detected signal.

23. An apparatus as recited in claim 1 wherein the resonance coil is arranged such that the fluid passing through the tube passes through the turns of the resonance coil.

24. An apparatus as recited in claim 4 wherein the frequency of the signal produced by the signal generator is in the range of approximately 10–100 MHz, the apparatus further comprising processing means for processing the detected signal and outputting an indicia indicative of the ionic concentration of the fluid being monitored.

25. An apparatus for determining the concentration of an acidic solution used in a wafer wet cleaning step of a semiconductor fabrication process, the apparatus comprising:
means for automatically detecting the ionic concentration of the solution wherein the ionic concentration determining means includes,
a housing arranged to receive a tube that is capable of passing the fluid there through,
a signal generator for providing a high frequency excitation signal,
an excitation coil wrapped around a portion of the tube, the excitation coil being connected to the signal generator,
a resonance coil wrapped around a length of the tube, the resonance coil being arranged for inductive communication with the excitation coil, and
detecting means for measuring the losses experienced by the resonance coil;
means for automatically detecting the density of the solution; and
processing means for determining the concentration of the wafer cleaning solution based upon information provided by the ionic concentration detecting means and the density detecting means.

26. A apparatus for detecting the ionic concentration of a fluid, the apparatus comprising:
a receiver located in the region of the fluid being monitored;
a signal generator for providing a high frequency electromagnetic signal;
means for applying the high frequency electromagnetic signal to the receiver;
detecting means for measuring a resultant signal that is received by the receiver and outputting a detected signal indicative of the magnitude of the resultant signal; and
processing means for processing the detected signal and outputting an indicia indicative of the ionic concentration of the fluid being monitored.

27. An apparatus as recited in claim 26 wherein the frequency of the signal produced by the signal generator is in the range of approximately 10–100 MHz.

28. An apparatus as recited in claim 26 wherein the frequency of the signal produced by the signal generator is in the range of approximately 30–80 MHz.

29. An apparatus as recited in claim 26 wherein the means for applying the signal in the region of the fluid being measured is an induction coil.

30. An apparatus as recited in claim 26 further comprising a resonance coil positioned in the vicinity of the fluid being monitored, the resonance coil being coupled to a capacitor means to form an LC circuit.

31. An apparatus as recited in claim 26 wherein the detector means for applying the high frequency signal includes an induction coil.

* * * * *